(12) United States Patent
Han et al.

(10) Patent No.: US 12,167,933 B2
(45) Date of Patent: Dec. 17, 2024

(54) METHOD FOR ULTRASOUND IMAGING AND RELATED EQUIPMENT

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventors: Xiao Han, Shenzhen (CN); Yaoxian Zou, Shenzhen (CN); Muqing Lin, Shenzhen (CN); Tianzhu Liang, Shenzhen (CN); Wenfang Wang, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 460 days.

(21) Appl. No.: 17/174,258

(22) Filed: Feb. 11, 2021

(65) Prior Publication Data
US 2021/0251601 A1    Aug. 19, 2021

Related U.S. Application Data

(63) Continuation of application No. PCT/CN2018/101791, filed on Aug. 22, 2018.

(51) Int. Cl.
*A61B 8/08* (2006.01)
*A61B 8/00* (2006.01)
*G06T 15/08* (2011.01)

(52) U.S. Cl.
CPC ............. *A61B 8/085* (2013.01); *A61B 8/466* (2013.01); *A61B 8/469* (2013.01); *A61B 8/483* (2013.01);
(Continued)

(58) Field of Classification Search
CPC ......... A61B 8/085; A61B 8/466; A61B 8/469; A61B 8/483; A61B 8/523; G06T 15/08;
(Continued)

(56) References Cited

U.S. PATENT DOCUMENTS 9,460,499 B2    10/2016  McLaughlin et al.
2014/0152649 A1*  6/2014  Moeller .................. G06T 19/00
                                                                              345/419

(Continued)

FOREIGN PATENT DOCUMENTS

CN       105263420 A     1/2016
CN       106102585 A    11/2016
(Continued)

OTHER PUBLICATIONS

PCT International Search Report and the Written Opinion mailed Dec. 24, 2018, issued in related International Application No. PCT/CN2018/101791, with partial English translation (9 pages).

(Continued)

*Primary Examiner* — Baisakhi Roy
*Assistant Examiner* — Kaitlyn E Sebastian
(74) *Attorney, Agent, or Firm* — Sheppard Mullin Richter & Hampton LLP (57) ABSTRACT

The present disclosure relates to a method for ultrasound imaging and a related equipment, the method for ultrasound imaging comprising: obtaining ultrasound body data of a test object; determining position information of a target anatomical structure from the ultrasound body data; determining an ultrasound image of the target anatomical structure from the ultrasound body data according to the position information of the target anatomical structure; and displaying the ultrasound image.

18 Claims, 7 Drawing Sheets

(52) U.S. Cl.
CPC .............. *A61B 8/523* (2013.01); *G06T 15/08* (2013.01); *G06T 2210/41* (2013.01)

(58) Field of Classification Search
CPC ................. G06T 2210/41; G06T 5/008; G06T 2207/10136; G06T 2207/30016; G06T 5/40; G06T 7/73
See application file for complete search history.

(56) References Cited

U.S. PATENT DOCUMENTS

| | | | | |
|---|---|---|---|---|
| 2015/0348247 | A1* | 12/2015 | McLaughlin | G06T 5/009 382/131 |
| 2016/0038121 | A1* | 2/2016 | Waechter-Stehle | G06T 7/10 600/443 |
| 2016/0051220 | A1* | 2/2016 | Lee | G06T 7/149 600/453 |
| 2017/0367685 | A1* | 12/2017 | Zou | G06F 18/22 |
| 2020/0034997 | A1* | 1/2020 | Zeng | G06T 5/40 |
| 2020/0297321 | A1 | 9/2020 | Waechter-Stehle et al. | |

FOREIGN PATENT DOCUMENTS

| | | | | |
|---|---|---|---|---|
| CN | 106659468 | A | 5/2017 | |
| CN | 106102585 | B * | 7/2019 | ........... A61B 8/0808 |
| EP | 2386251 | A1 | 11/2011 | |
| EP | 3040031 | A1 | 7/2016 | |

OTHER PUBLICATIONS

PCT International Preliminary Report on Patentability mailed Mar. 4, 2021, issued in related International Application No. PCT/CN2018/101791, with English translation (11 pages).

First Search dated Mar. 24, 2022, issued in related Chinese Application No. 201880096078.4 (3 pages).

* cited by examiner

METHOD FOR ULTRASOUND IMAGING AND RELATED EQUIPMENT

This application is a continuation application of International Patent Application No. PCT/CN2018/101791, filed with the China National Intellectual Property Administration (CNIPA) on Aug. 22, 2018. The content of the above application is incorporated herein by reference in its entirety.

TECHNICAL FIELD

The present disclosure relates to medical imaging, and in particular to an ultrasound imaging method and a device using the same.

BACKGROUND

With the development of science and technology, more and more doctors use an ultrasound instrument to observe the internal tissue structure of a human body. When using the ultrasound instrument for detection, a doctor places an ultrasonic probe on the corresponding skin surface of a part of the human body to obtain an ultrasound image of the part.

In recent years, ultrasonography has been widely applied clinically, in which complete image information can be obtained with one scan using the ultrasound instrument. However, since an image region obtained is relatively large, the ultrasound instrument needs to receive a plurality of position adjustment instructions sent from an operator so as to obtain a correct display position of the image, which results in a long operating time of the ultrasound instrument, and wastes ultrasound instrument resources.

SUMMARY

In one embodiment, an ultrasound imaging method and a device using the same are provided.

In one embodiment, an ultrasound imaging method is provided, which may include:
  obtaining ultrasound volume data of an object;
  determining position information of a target anatomical structure from the ultrasound volume data;
  determining an ultrasound image of the target anatomical structure from the ultrasound volume data according to the position information of the target anatomical structure; and
  displaying the ultrasound image.

In one embodiment, a method for optimizing ultrasound volume data is provided, which may include:
  obtaining ultrasound volume data of an object;
  determining position information of a target anatomical structure from the ultrasound volume data; and
  optimizing the ultrasound volume data according to the position information of the target anatomical structure.

In one embodiment, a method for optimizing an ultrasound image is provided, which may include:
  obtaining ultrasound volume data of an object;
  determining position information of a target anatomical structure from the ultrasound volume data;
  determining an ultrasound image of the target anatomical structure from the ultrasound volume data according to the position information of the target anatomical structure; and
  optimizing the ultrasound image.

In one embodiment, an ultrasound imaging system is provided, which may include:
  an ultrasonic probe configured to transmit ultrasound waves to an object and receive ultrasound echoes to obtain ultrasound signals;
  a memory storing computer-readable instructions;
  a processor, where the computer-readable instructions, when executed by the processor, may cause the processor to: process the ultrasound signals to obtain ultrasound volume data corresponding to the object; determine position information of a target anatomical structure from the ultrasound volume data; and determine an ultrasound image of the target anatomical structure from the ultrasound volume data according to the position information of the target anatomical structure; and
  a display configured to display the ultrasound image.

In one embodiment, an ultrasound imaging system is provided, which may include:
  an ultrasonic probe configured to transmit ultrasound waves to an object and receive ultrasound echoes to obtain ultrasound signals;
  a memory storing computer-readable instructions; and
  a processor, where the computer-readable instructions, when executed by the processor, may cause the processor to: process the ultrasound signals to obtain ultrasound volume data corresponding to the object; determine position information of a target anatomical structure from the ultrasound volume data; and optimize the ultrasound volume data according to the position information of the target anatomical structure.

In one embodiment, an ultrasound imaging system is provided, which may include:
  an ultrasonic probe configured to transmit ultrasound waves to an object and receive ultrasound echoes to obtain ultrasound signals;
  a memory having computer-readable instructions stored therein; and
  a processor, where the computer-readable instructions, when executed by the processor, may cause the processor to: process the ultrasound signals to obtain ultrasound volume data corresponding to the object; determine position information of a target anatomical structure from the ultrasound volume data; determine an ultrasound image of the target anatomical structure from the ultrasound volume data according to the position information of the target anatomical structure; and optimize the ultrasound image.

Details of one or more embodiments of the present disclosure are set forth in the accompanying drawings and description below. Other features, objectives and advantages of the present disclosure will be apparent from the description, the drawings and the claims.

BRIEF DESCRIPTION OF THE DRAWINGS

In order to illustrate the technical solutions in the embodiments of the present disclosure more clearly, drawings of the embodiments will be briefly introduced below. Obviously, the drawings in the following description are merely some of the embodiments of the present disclosure, and those of ordinary skill in the art will be able to obtain other drawings according to these drawings without involving any inventive effort.

DESCRIPTION OF THE PREFERRED EMBODIMENTS

In order to make the objective, technical solutions, and advantages of the present disclosure clearer, the present disclosure will be further described below in conjunction with the accompanying drawing and the embodiments. It should be understood that the specific embodiments described here are merely intended to explain the present disclosure but not intended to limit the present disclosure.

It can be understood that although the terms "first", "second", etc. used in the present disclosure may be used herein to describe various elements, these elements are not limited by these terms, unless otherwise specified. These terms are merely used to distinguish an element from another element. For example, a first threshold may be referred to as a second threshold and similarly, the second threshold may be referred to as the first threshold, without departing from the scope of the present disclosure.

Figure 1:
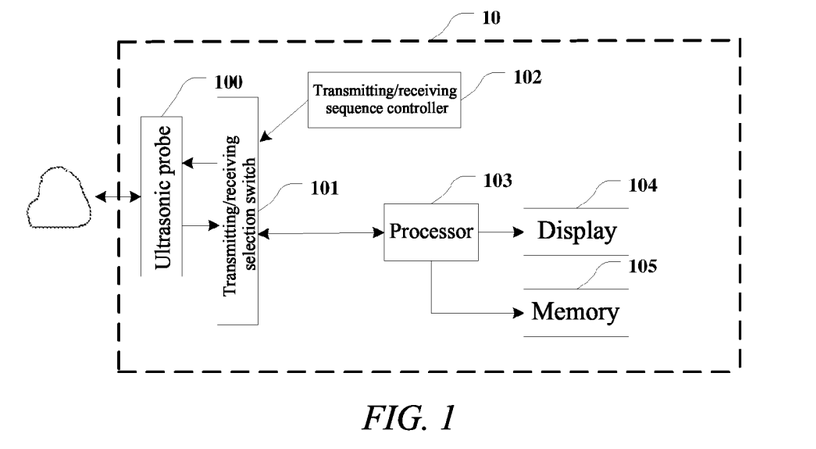
FIG. 1 is a structural block diagram of an ultrasound imaging system in one embodiment.

FIG. 1 is a corresponding structural block diagram of an ultrasound imaging system 10. The ultrasound imaging system 10 may comprise an ultrasonic probe 100, a transmitting/receiving selection switch 101, a transmitting/receiving sequence controller 102, a processor 103 and a display 104. The transmitting/receiving sequence controller 102 can excite the ultrasonic probe 100 to transmit ultrasound waves to an object, and can also control the ultrasonic probe 100 to receive ultrasound echoes returned from the object, so as to obtain ultrasound echo signals/data. The processor 103 processes the ultrasound echo signals/data to obtain ultrasound volume data of the object, and to determine ultrasound images of a target anatomical structure from the ultrasound volume data. The ultrasound images obtained by the processor 103 may be stored in a memory 105, and these ultrasound images may be displayed on the display 104.

In the embodiment of the present disclosure, the foregoing display 104 of the ultrasound imaging system 10 may be a touch display screen, a liquid crystal display screen, etc., or may be an independent display device, such as a liquid crystal display or a television, independent of the ultrasound imaging system 10, or may be a display screen on an electronic device, such as a mobile phone and a tablet computer.

In the embodiment of the present disclosure, the foregoing memory 105 of the ultrasound imaging system 10 may be a flash memory card, a solid state memory, a hard disk, etc.

In an embodiment of the present disclosure, further provided is a computer-readable storage medium, wherein the computer-readable storage medium stores a plurality of program instructions, and after the plurality of program instructions are invoked and executed by the processor 103, some or all of, or any combination of the steps in the following method embodiments of the present disclosure can be performed.

In an embodiment, the computer-readable storage medium may be the memory 105, which may be a non-volatile storage medium, such as a flash memory card, a solid state memory, and a hard disk.

In the embodiment of the present disclosure, the foregoing processor 103 of the ultrasound imaging system 10 may be implemented by software, hardware, firmware, or a combination thereof, and may use circuits, single or a plurality of application specific integrated circuits (ASICs), single or a plurality of universal integrated circuits, single or a plurality of microprocessors, single or a plurality of programmable logic devices, or a combination of the above circuits or devices, or other suitable circuits or devices, such that the processor 103 can perform the corresponding steps of the following method embodiments.

Figure 2:
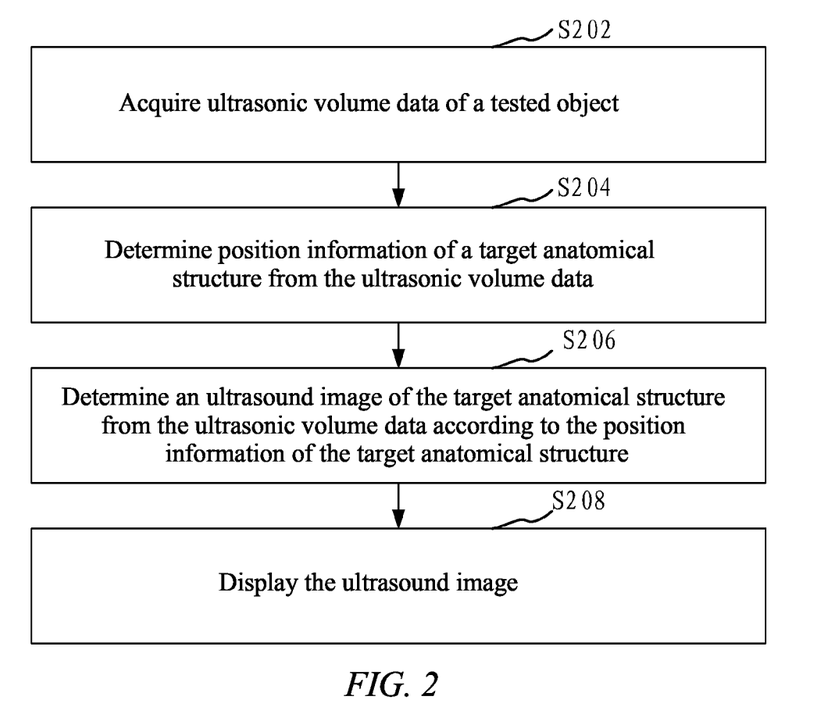
FIG. 2 is a flowchart of an ultrasound imaging method in one embodiment.

As shown in FIG. 2, in an embodiment, an ultrasound imaging method is provided, which may specifically comprise the steps as follows.

Step S202: Ultrasound volume data of an object is acquired.

Figure 3:
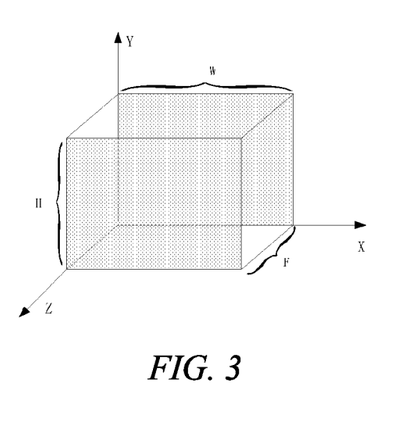
FIG. 3 is a schematic diagram of three-dimensional volume data in one embodiment.

In the embodiment of the present disclosure, the ultrasound volume data may be three-dimensional volume data or four-dimensional volume data. The three-dimensional volume data is a data set that reflects positions of pixels in an image in three-dimensional space coordinates, and each position corresponds to one pixel and has a corresponding pixel value. The four-dimensional volume data is implemented by adding a dimension of time to the three-dimensional volume data, i.e., the four-dimensional volume data is three-dimensional volume data that changes over time, which can dynamically reflect the activity of an object. FIG. 3 is a schematic diagram of three-dimensional volume data. It can be seen from FIG. 3 that the volume data may be composed of F image frames with a size of W×H, where W is the width of the image frame, H is the height of the image frame, and the specific value of F may be any integer greater than or equal to 2. In addition, it can be seen from FIG. 3 that the width direction of the image frame is defined as the X direction, the height direction of the image frame is defined as the Y direction, and the direction in which a plurality of image frames are arranged is defined as the Z direction in FIG. 3. It can be understood that the X, Y, and Z directions may also be defined in different ways. The object may be various tissues and organs of humans or animals, etc. It is set as required, for example, the object may be one or more of the pelvic floor, endometrium, fetal heart, adult heart, liver, and fetal brain. The ultrasonic probe 100 in the ultrasound imaging system 10 can be used to perform three-dimensional scanning on the object and transmit ultrasound waves to the object, and the ultrasonic probe 100 receives ultrasound echoes to obtain ultrasound echo signals, which are then processed by the processor 103 as described above, so as to obtain ultrasound volume data of the object. The ultrasound volume data may be obtained by sending ultrasound waves to an object in real time, or may be pre-stored in a memory of the ultrasound imaging system.

Step S204: Position information of a target anatomical structure is determined from the ultrasound volume data.

After the ultrasound volume data is obtained, in the embodiment of the present disclosure, the processor 103 can detect the target anatomical structure in the object from the ultrasound volume data automatically or by receiving an instructions input by a user, and the processor 103 determines an ultrasound image corresponding to the target anatomical structure according to the position information of the target anatomical structure, so as to provide good image information and analysis data to a doctor in real time.

In the embodiment of the present disclosure, there may be one or more target anatomical structures, and more may refer to two or more, and the specific value may be set as required. The target anatomical structure for which the position information needs to be determined is related to the type of the object and an image that needs to be viewed. For example, in pelvic floor data, anatomical structures such as the pubic symphysis, a vaginal gas line and anorectal angle are relatively obvious, and at least one of the above anatomical structures can be found and identified as the target anatomical structure; for another example, in endometrial volume data, echoes of the endometrium are significantly different from echoes of surrounding tissues, and the features are relatively obvious, such that the endometrium can be segmented as the target anatomical structure; for another example, in fetal brain volume data, features of anatomical structures such as the craniocerebral aura, sagittal plane, cerebellum, and cavity of septum pellucidum are relatively obvious, and at least one of the above anatomical structures can be found and identified as the target anatomical structure; for another example, in fetal heart volume data, anatomical structures such as the aorta, four-chamber, and magenblase are relatively obvious, and at least one of the above anatomical structures can be found and identified as the target anatomical structure. Each target anatomical structure for which the position information needs to be determined, which corresponds to the object, may be preset or obtained in real time according to the user's selection. For example, the target anatomical structures to be obtained from the pelvic floor are preset as the craniocerebral aura, sagittal plane, and cerebellum, and after ultrasound volume data is obtained, the processor of the ultrasound imaging system can determine the position information of the target anatomical structure from the ultrasound volume data.

In an embodiment, the determining position information of a target anatomical structure from the ultrasound volume data comprises: obtaining identification information for identifying the target anatomical structure; and determining the position information of the target anatomical structure from the ultrasound volume data according to the identification information.

In the embodiment of the present disclosure, the identification information is information used to identify the target anatomical structure from the ultrasound volume data. For example, it is possible to display an ultrasound image corresponding to the ultrasound volume data, receive an identification operation for identifying the target anatomical structure, such as a click operation or a sliding operation of a user such as a doctor with regard to the ultrasound image by means of an input tool such as a keyboard or a mouse, and use the position corresponding to the identification operation as the position of the target anatomical structure; further, it is also possible to obtain a name of the target anatomical structure corresponding to the position. The name of the target anatomical structure may be the received input from the user.

In an embodiment, the determining position information of a target anatomical structure from the ultrasound volume data comprises: obtaining structural feature information of the target anatomical structure; and determining the position information of the target anatomical structure from the ultrasound volume data according to the structural feature information.

In the embodiment of the present disclosure, the target anatomical structure has a corresponding unique structural feature. For example, the cavity of septum pellucidum in the brain is shaped like a crescent. The magenblase structure in the fetal heart usually appears as a hypoechoic or anechoic ellipsoid. Therefore, structural feature information corresponding to all the anatomical structures can be preset. When the target anatomical structure needs to be identified, the structural feature information of the target anatomical structure is obtained for matching in the ultrasound volume data, and the position information of the anatomical structure that is obtained by matching is used as the position information of the target anatomical structure. For the identification method, one or more of an image segmentation method or a template matching method can be used. For example, the image segmentation method can be used to obtain magenblase by segmentation. First, binary segmentation and morphological operations are performed on the ultrasound volume data according to grayscale data, so as to obtain a plurality of candidate regions, and then the probability that each candidate region is the magenblase is determined according to features such as the shape, and the region with the highest probability is selected as a magenblase region. Other image segmentation methods can also be used, such as one or more of a level set method, graph cut, a snake model, random walker, and a deep learning image segmentation method. The deep learning image segmentation method may be, e.g., one or more of fully convolutional networks (FCNs) or unity networking (UNet). For another example, the template matching method can be used to identify and obtain the cavity of septum pellucidum in the brain. Some grayscale data of the cavity of septum pellucidum can be pre-collected to establish a template, and then matching is performed between grayscale data of each image region of the ultrasound volume data and the grayscale data of the template to select a region with a high similarity as the region corresponding to the target anatomical structure, wherein the ultrasound volume data may be divided into a plurality of regions matching the template, and a method for region division of the image corresponding to the ultrasound volume data may be set as needed. The similarity is used to measure the similarity between each region in the template and each image region in the ultrasound volume data. When the similarity is higher, it indicates a higher possibility of the image region being the target anatomical structure. Therefore, the region with the highest similarity can be used as the region corresponding to the target anatomical structure. A similarity calculation method may be set as required. For example, the similarity may be the sum of absolute values of differences between grayscale values of pixels in the template and pixels in the image region. It is expressed with the following formula:

$$E=\Sigma_1^H |I_L - I_R|$$

where E is the similarity, $I_L$ is the grayscale value of the pixel in the image region corresponding to the ultrasound volume data, and $I_R$ is the grayscale value of the pixel in the template. H is the number of pixels in the template, and $I_L-I_R$ means the subtraction of the grayscale values of the pixels in the template and the pixels in the image region at the same positions. It can be understood that the similarity can be determined by using other methods, such as an Euclidean distance between the region in the template and the image region corresponding to the ultrasound body, and a cosine similarity between the region in the template and the image region corresponding to the ultrasound volume. The present disclosure is not limited to how to define the above specific similarity calculation method, and any calculation methods on the basis of measuring the similarity between the region in the template and the image region corresponding to the ultrasound volume can be used in the embodiments of the present disclosure.

In an embodiment, the position information of the target anatomical structure can also be obtained through identification by using a machine learning model. The machine learning model may be a learning model obtained through training based on one or more of an Adaboost algorithm, a support vector machine (SVM), a neural network algorithm, a convolutional neural network 20 (CNN) algorithm, a recursive neural network (RNN) algorithm, a fast Region-based Convolutional Network (RCNN), and a single shot multibox detector (SSD). During model training, a supervised learning method can be used to learn feature extraction parameters in a machine learning network, such that a mapping from the ultrasound volume data to the position information of the target anatomical structure can be established. Positive samples and negative samples used for model training can be collected. By 25 using the positive samples and the negative samples for model training, model parameters that can distinguish the positive samples from the negative samples can be obtained, so as to obtain an anatomical structure recognition model. Then the ultrasound volume data is input into the anatomical structure recognition model to obtain a probability that each image region corresponding to the ultrasound volume data is a target anatomical sample, and a region with the highest probability is selected as the region corresponding to the target anatomical structure. The positive sample is a sample that is the target anatomical structure, and the negative sample is a sample that is not the target anatomical structure.

Step S206: An ultrasound image of the target anatomical structure is determined from the ultrasound volume data according to the position information of the target anatomical structure.

In the embodiment of the present disclosure, the ultrasound image of the target anatomical structure comprises all or part of the target anatomical structure. The ultrasound image of the target anatomical structure may be one or both of an ultrasound image of a cross section corresponding to the target anatomical structure and an ultrasound image of a volume of interest corresponding to the target anatomical structure. The cross section corresponding to the target anatomical structure is a cross section comprising all or part of the target anatomical structure, and the volume of interest corresponding to the target anatomical structure contains all or part of the target anatomical structure. After the target anatomical structure is obtained, the processor 103 determines an image region comprising the target anatomical structure according to the position information of the target anatomical structure, and extracts the image corresponding to the region from the ultrasound volume data, so as to obtain the ultrasound image.

In an embodiment, the processor 103 may select a plurality of feature points from the target anatomical structure, and fit the plurality of feature points to obtain a cross section equation corresponding to the cross section, thereby obtaining a target cross section. The determination of a plane according to a plurality of feature points can be realized by using a plurality of methods, such as at least one of a weighted Hough transform method, a random Hough transform method, a least squares estimation method and a Radon transform method. The feature point may be any one or a plurality of feature points selected from each target anatomical structure. The position for selection may be set as required. For example, a center point of each target anatomical structure may be used as a feature point.

For example, the cross section of the cerebellum in the brain contains anatomical structures such as the cerebellum, cavity of septum pellucidum and thalamus. Therefore, one position point can be selected from each of the cerebellum, cavity of septum pellucidum and thalamus to obtain three position points, and the three position points are not collinear, such that the plane can be determined according to the principle that a unique plane can be formed by three non-collinear points, thereby making it possible for the plane to pass through each target anatomical structure.

Step S208: The ultrasound image is displayed.

In the embodiment of the present disclosure, after the ultrasound image is obtained, the ultrasound image is displayed on the display 104 in the ultrasound imaging system 10.

According to the above ultrasound imaging method, since the corresponding ultrasound image can be determined according to the position of the target anatomical structure, the time for obtaining the ultrasound image is reduced, and ultrasound instrument resources are saved. Moreover, the above ultrasound imaging method also makes it possible to provide a more precisely positioned ultrasound image to a doctor so that the doctor can conveniently observe the ultrasound image of an object, to provide a large amount of important key information to the doctor and to improve the working efficiency.

Figure 4:
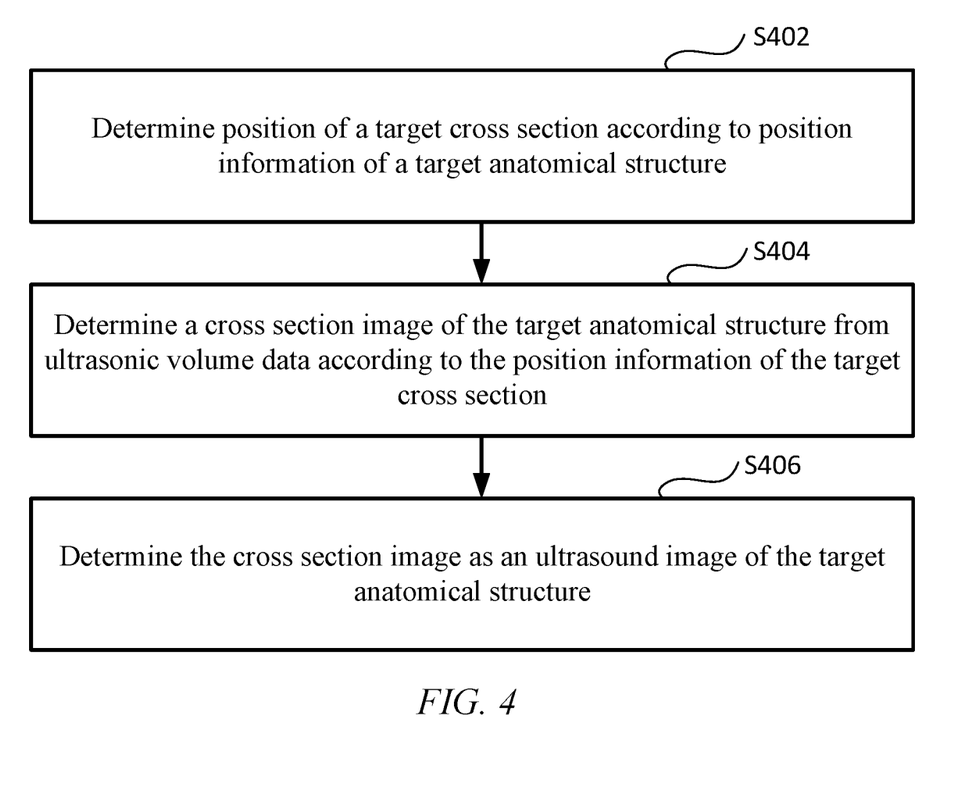
FIG. 4 is a flowchart of determining an ultrasound image of a target anatomical structure from the ultrasound volume data according to position information of the target anatomical structure in one embodiment.

In an embodiment step S206 of determining an ultrasound image of the target anatomical structure from the ultrasound volume data according to the position information of the target anatomical structure comprises the steps shown in FIG. 4, which comprise the following steps.

Step S402: Position information of a target cross section is determined according to the position information of the target anatomical structure.

In the embodiment of the present disclosure, the target cross section is a cross section comprising all or part of the target anatomical structure. After the target anatomical structure is obtained, the target cross section can be determined according to a preset method. For example, a traversal method can be used to traverse to obtain candidate sections that can pass through each target anatomical structures, and then to select, from the candidate sections, the candidate section comprising the largest region of the target anatomical structure as the target cross section. Alternatively, if the region, which is occupied by each target anatomical structure, in a candidate section obtained during traversal is greater than a preset threshold, the candidate section is used as the target cross section, and the traversal is stopped.

In an embodiment, the determining position information of a target cross section according to the position information of the target anatomical structure comprises: determining an equation of the target cross section according to the position information of the target anatomical structure; and obtaining the position information of the target cross section according to the equation of the target cross section.

In the embodiment of the present disclosure, in a three-dimensional space, the plane equation may be expressed with $aX+bY+cZ+d=0$ or $\rho=\cos\theta\cos\varphi X+\sin\theta\cos\varphi Y+\sin\varphi Z$, where a, b, c and d are plane parameters that determine a plane, or $\theta$, $\varphi$, $\rho$ is a plane parameter. After the position information of the target anatomical structure is obtained, one or more feature points can be selected from the target anatomical structure, and position information of the feature points is substituted into the plane equation to solve the plane parameter and obtain a section function corresponding to the target cross section, and a region corresponding to the cross section function is obtained from ultrasound volume data, so as to obtain the position information corresponding to the target cross section.

In an embodiment, the equation of the target cross section can be determined according to the position information of the three sub-target anatomical structures by using three non-collinear points.

In the embodiment of the present disclosure, if there are three target anatomical structures, one position point can be obtained from each of the three target anatomical structures to obtain three position points that are not collinear. Therefore, the equation of the target cross section can be determined according to the position information of the three target anatomical structures by using three non-collinear points. That is to say, the position information corresponding to each position point can be substituted into the cross section equation, which is then solved for an equation of the target cross section, i.e., a section function, wherein the cross section in the ultrasound volume data that corresponds to the cross section function is the target cross section. The method for obtaining position points from the target anatomical structure may be set as required, for example, a center point of each target anatomical structure may be obtained.

In an embodiment, if there are at least four target anatomical structures, the equation of the target cross section can be determined according to position information of the at least four target anatomical structures by means of fitting, wherein the fitting comprises at least one of least squares estimation and Hough transform.

In the embodiment of the present disclosure, the least squares method is a mathematical optimization technique. It finds the best function match of data by minimizing the sum of squares of the error. By using the least squares method, unknown data can be easily solved, and the sum of squares of the errors between the solved data and actual data is made to be less than a preset value. The principle of Hough transform is to transform points on a specific graph to a group of parameter spaces, and to find a solution corresponding to a maximal value according to a cumulative result of the points in the parameter spaces, and then this solution corresponds to a geometry parameter to be sought for. Since there are four or more target anatomical structures, there are four or more feature points obtained. Four or more non-collinear feature points can determine a plurality of sections. Therefore, the equation of the target cross section can be determined according to the position information of the at least four target anatomical structures by means of fitting. When the least squares estimation is used for fitting, feature points can be selected from each target anatomical structure to obtain function parameters corresponding to the cross section, and then, when the step of selecting the feature points to obtain the function parameters is repeated until the sum of squares of errors between the solved data and actual data is less than a preset value or the number of repetitions reaches a preset number of times, the finally obtained function parameters are used as the parameters of the cross section equation. When the Hough transform is used for fitting, feature points can be selected from each target anatomical structure, position information of the feature points is used to solve function parameters corresponding to the cross section, and a Hough matrix is updated with the function parameters, and then, when the steps of selecting the feature points to obtain the function parameters and updating the Hough matrix with the function parameters are repeated until the number of repetitions reaches a preset number of times, a function parameter corresponding to the maximum value in the Hough matrix is calculated to obtain a final function value according to the function parameter. The preset number of times may be set as required, e.g., to 10,000 times.

Step S404: A cross section image of the target anatomical structure is determined from the ultrasound volume data according to the position information of the target cross section.

Step S406: The cross section image is determined as the ultrasound image of the target anatomical structure.

In the embodiment of the present disclosure, after the position information of the target cross section is obtained, the processor 103 obtains a grayscale value of a pixel corresponding to the position information in the ultrasound volume data to obtain a cross section image, which is then used as the ultrasound image of the target anatomical structure.

Figure 5:
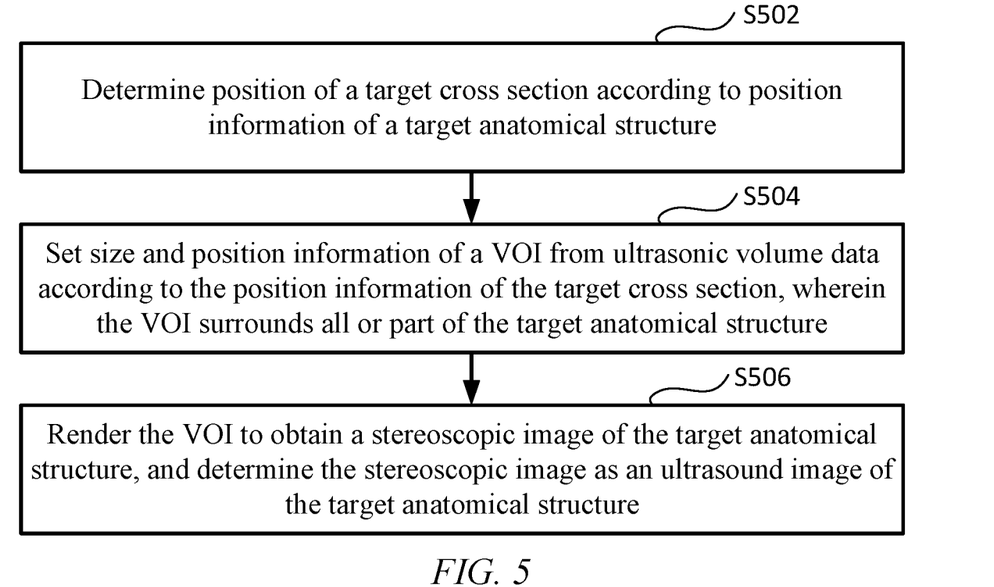
FIG. 5 is a flowchart of determining an ultrasound image of a target anatomical structure from the ultrasound volume data according to position information of the target anatomical structure in one embodiment.

In an embodiment step S206 of determining an ultrasound image of the target anatomical structure from the ultrasound volume data according to the position information of the target anatomical structure may specifically comprise the steps shown in FIG. 5, which comprise the following steps.

Step S502: Position information of a target cross section is determined according to the position information of the target anatomical structure.

In the embodiment of the present disclosure, for the determining of position information of a target cross section according to the position information of the target anatomical structure, reference may be made to the description in step S402. The embodiment of the present disclosure will not be repeated in detail herein.

Step S504: Size and position information of a volume of interest (VOI) is set from the ultrasound volume data according to the position information of the target cross section, wherein the VOI contains all or part of the target anatomical structure.

In the embodiment of the present disclosure, the volume of interest (VOI) is a region of a stereoscopic image that needs to be viewed. The size of the VOI refers to dimensions of the VOI. For example, the dimensions of the VOI in three directions of length, width, and height may be set. The size and position information of the VOI may be determined according to the position information of the target cross section, so that the VOI contains all or part of the target anatomical structure. For example, a volume threshold can be preset, and the proportion of the volume corresponding to the target anatomical structure surrounded by the VOI to the total volume of the target anatomical structures is set to be greater than the set volume threshold. Therefore, after the position information of the target cross section is obtained, the size and position information of the volume of interest (VOI) are adjusted in the ultrasound volume data, such that the proportion of the volume of the target anatomical structure surrounded by the VOI to the total volume of the target anatomical structures is greater than the preset volume threshold.

Step S506: The VOI is rendered to obtain a stereoscopic image of the target anatomical structure, and the stereoscopic image is determined as the ultrasound image of the target anatomical structure.

In the embodiment of the present disclosure, after the VOI is obtained, the processor 103 performs rendering according to grayscale values of pixels corresponding to the VOI to obtain a stereoscopic image, wherein the stereoscopic image is used as the ultrasound image of the target anatomical structure.

The method provided in the embodiment of the disclosure will be described below by taking an actual object as an example. In the detection of a cerebellar section, a spatial position of the cerebellar section is calculated according to the positions of the target anatomical structures such as the craniocerebral aura, cerebellum and cavity of septum pellucidum, so as to obtain the corresponding cerebellar section; on this basis, the size and position of the VOI are set, such that VOI encloses at least one target anatomical structure such as the craniocerebral aura, cerebellum and cavity of septum pellucidum to obtain a stereoscopic image of the cerebellar section, i.e., the image corresponding to the VOI. For another example, in imaging of the pelvic floor levator ani hiatus, positions of target structures such as the lower edge of the pubic symphysis and the anorectal angle are identified, and both the lower edge of the pubic symphysis and the anorectal angle are automatically rotated to the same horizontal position according to the positions of the two; the VOI is adjusted such that the VOI just contains the lower edge of the pubic symphysis and the anorectal angle, and then the VOI is rendered to obtain a levator ani hiatus image. For another example, in endometrium imaging, the position of the endometrium is identified; according to the position of the endometrium, a VOI curve is adjusted to coincide with a lower edge of the endometrium by adjusting the volume data orientation and the VOI, and then a region corresponding to the VOI is rendered to obtain a stereoscopic image.

Figure 6:
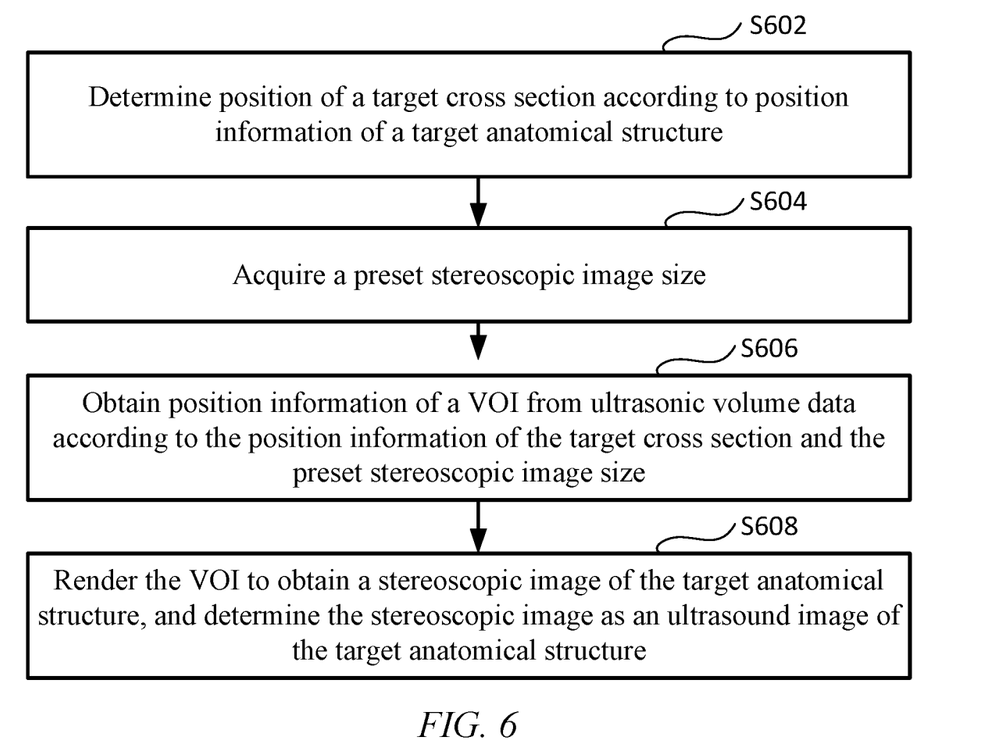
FIG. 6 is a flowchart of determining an ultrasound image of a target anatomical structure from the ultrasound volume data according to position information of the target anatomical structure in one embodiment.

In an embodiment step S206, i.e., the step of determining an ultrasound image of the target anatomical structure from the ultrasound volume data according to the position information of the target anatomical structure, may specifically comprise the steps shown in FIG. 6, which comprise the following steps.

Step S602: Position information of a target cross section is determined according to the position information of the target anatomical structure.

In the embodiment of the present disclosure, for the determining of position information of a target cross section by the processor 103 according to the position information of the target anatomical structure, reference may be made to the description in step S402. The embodiment of the present disclosure will not be repeated in detail herein.

Step S604: A preset stereoscopic image size is obtained.

In the embodiment of the present disclosure, the stereoscopic image size is preset. The specific size can be set as needed. For example, when an object is subjected to the pelvic floor levator ani hiatus, the VOI can be set to 2 cm in length, width and height.

Step S606: Position information of the VOI is obtained from the ultrasound volume data according to the position information of the target cross section and the preset stereoscopic image size.

In the embodiment of the present disclosure, the target cross section is in the volume of interest (VOI). With the target cross section as the center, the target cross section may be extended in each spatial dimension according to the preset stereoscopic image size, so as to obtain the volume of interest (VOI). For example, assuming that the VOI is 2 cm in length, width and height, then, in ultrasound volume data, with a center point of the target cross section as the center, the target cross section is extended by 1 cm respectively in the positive direction of the X axis, the negative direction of the X axis, the positive direction of the Y axis, the negative direction of the Y axis, the positive direction of the Z axis, and the negative direction of the Z-axis to obtain position information of the VOI.

Step S608: The VOI is rendered to obtain a stereoscopic image of the target anatomical structure, and the stereoscopic image is determined as the ultrasound image of the target anatomical structure.

In the embodiment of the present disclosure, after the VOI is obtained, the processor 103 renders a region corresponding to the VOI to obtain a stereoscopic image, wherein the stereoscopic image is used as the ultrasound image of the target anatomical structure.

Figure 7:
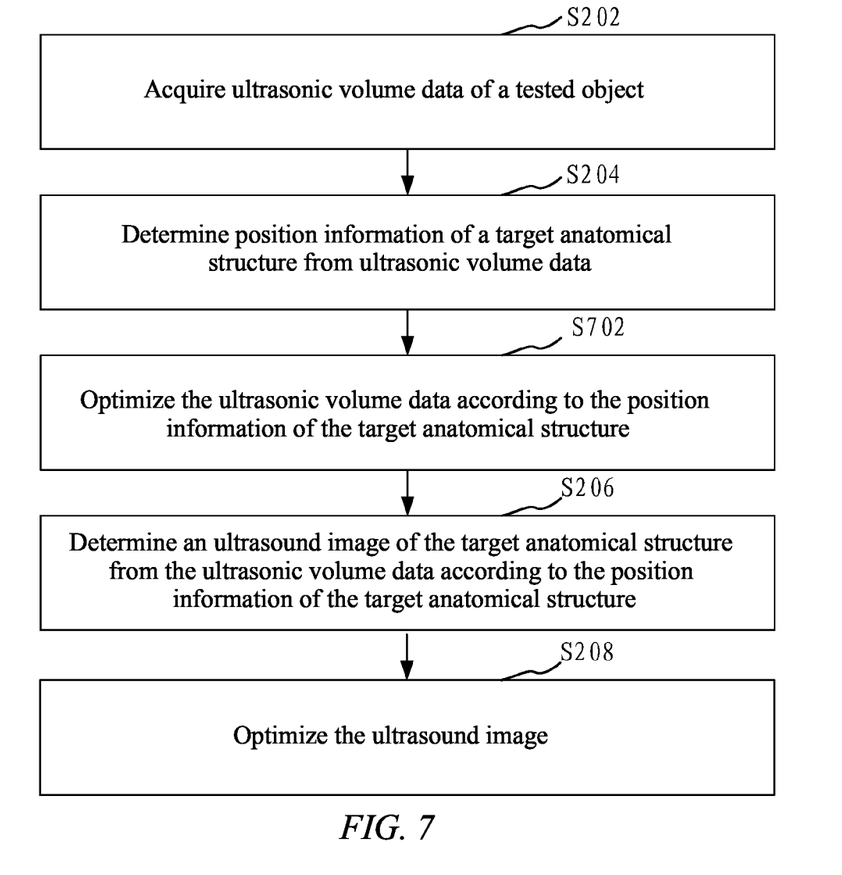
FIG. 7 is a flowchart of an ultrasound imaging method in one embodiment.

In an embodiment, as shown in FIG. 7, after the processor 103 determines the position information of the target anatomical structure from the ultrasound volume data, the ultrasound imaging method may further comprise step S702: optimizing the ultrasound volume data according to the position information of the target anatomical structure.

In the embodiment of the present disclosure, after the position information of the target anatomical structure is obtained, the processor 103 may determine an optimized target position region according to the position information of the target anatomical structure, and optimize ultrasound volume data corresponding to the target position region. For example, the target position region may be a region corresponding to the target cross section, or may be a region corresponding to the VOI. A grayscale value may be optimized. For example, the grayscale value is increased, or the grayscale value is decreased, etc. After the ultrasound volume data is optimized, the corresponding ultrasound image can be immediately displayed according to the ultrasound volume data obtained through optimization.

In one implementation, the processor 103 may decrease an ultrasound volume data parameter value of a non-target anatomical structure region according to the position information of the target anatomical structure, such that a difference between an ultrasound volume data parameter value of the target anatomical structure and the ultrasound volume data parameter value of the non-target anatomical structure region is within a preset range.

In the embodiment of the present disclosure, the ultrasound volume data parameter value may be a grayscale value. The preset range may be greater than a preset first threshold and less than a preset second threshold, wherein the second threshold is greater than the first threshold, and the specific range can be set as required. The non-target anatomical structure region is a region other than the target anatomical structure in the ultrasound volume data.

In an embodiment, an ultrasound volume data parameter value of a region corresponding to the target anatomical structure may also be improved, such that a difference between an ultrasound volume data parameter value of the target anatomical structure and the ultrasound volume data parameter value of the non-target anatomical structure region is within a preset range.

Since the target anatomical structure is usually a region of interest to a user, and the non-anatomical structure is usually located in a region with the background or noise to be suppressed., a grayscale value of a region other than the target anatomical structure region can be decreased or the grayscale value of the anatomical structure region itself can be increased according to the position of the target anatomical structure, so as to suppress noise, increase the signal strength of the target anatomical structure, and adaptively increase the contrast of the rendered image.

In an embodiment, the optimizing the ultrasound volume data according to the position information of the target anatomical structure comprises: obtaining ultrasound volume data parameter values of the target anatomical structure and a non-target anatomical structure region according to the position information of the target anatomical structure; and adjusting, as a whole, the ultrasound volume data parameter values of the target anatomical structure and the non-target anatomical structure region according to a preset condition.

In the embodiment of the present disclosure, the ultrasound volume data parameter value is a parameter related to the ultrasound volume data, such as a grayscale value. The preset condition may be that the difference between the ultrasound volume data parameter values of the target anatomical structure and the non-target anatomical structure region is within a preset range, the contrast is within the preset range, or the probability density of the grayscale corresponding to the ultrasound volume data is uniformly distributed, etc. The overall adjustment refers to the adjustment to both the ultrasound volume data parameter values corresponding to the target anatomical structure and the non-target anatomical structure region. According to the position information of the target anatomical structure, the non-target anatomical structure region and the region corresponding to the target anatomical structure can be obtained. In different regions, different adjustment strategies or adjustment values are adopted. For example, an average grayscale value of the ultrasound volume data can be counted, and the average grayscale value can be compared with a preset grayscale value. If the average grayscale value is less than the preset grayscale value, the grayscale value is increased, otherwise, the grayscale value is decreased. For another example, a histogram equalization method can be used to adjust the ultrasound volume data parameter values. Histogram equalization is a method that extends an image non-linearly and redistributes image pixels such that the number of pixels in a certain grayscale range is approximately the same.

In an embodiment, the processor 103 may adjust one or both of the ultrasound volume data parameter values of the target anatomical structure and the non-target anatomical structure region. For example, an average grayscale value corresponding to the target anatomical structure can be counted, and the average grayscale value corresponding to the target anatomical structure can be compared with a preset grayscale value. If the average grayscale value is less than the preset grayscale value, the grayscale value is increased, otherwise, the grayscale value is decreased.

In an embodiment, after step S206 of determining an ultrasound image of the target anatomical structure from the ultrasound volume data according to the position information of the target anatomical structure, the ultrasound imaging method further comprises: optimizing the ultrasound image.

In the embodiment of the present disclosure, the processor 103 optimizes parameters related to the ultrasound image, for example, may optimize at least one of a threshold, a gain, brightness, and contrast of the ultrasound image, wherein the threshold herein is a difference between grayscale values of the target anatomical structure and the non-target anatomical structure region, and the non-target anatomical structure region is a region other than the target anatomical structure in the ultrasound volume data. The difference between the grayscale values of the target anatomical structure and the non-target anatomical structure region may be a difference between the corresponding average grayscale values.

In an embodiment, optimizing the threshold of the ultrasound image may include obtaining the threshold of the ultrasound image and adjusting the threshold of the ultrasound image when the threshold of the ultrasound image is not in a preset threshold range.

In the embodiment of the present disclosure, the preset threshold range may be set as required. The preset threshold range may be greater than a preset third threshold and less than a preset fourth threshold, where the fourth threshold is greater than the third threshold. If the threshold of the ultrasound image does not satisfy the preset threshold range, one or both of the grayscale values of the target anatomical structure and the non-target anatomical structure region may be adjusted so that the obtained threshold satisfies the preset threshold range. For example, if the threshold of the ultrasound image is less than the third threshold, the grayscale value corresponding to the target anatomical structure may be increased or the grayscale value of the non-target anatomical structure region may be decreased. If the threshold of the ultrasound image is greater than the third threshold, the grayscale value corresponding to the target anatomical structure can be decreased.

In an embodiment, the optimizing at least one of the gain, the brightness, and the contrast of the ultrasound image by the processor 103 comprises: obtaining a signal strength value of the ultrasound image; decreasing at least one of the gain, the brightness, and the contrast of the ultrasound image if the signal strength value is greater than a preset value; and increasing at least one of the gain, the brightness, and the contrast of the ultrasound image if the signal strength value is less than a preset value.

In the embodiment of the present disclosure, the signal strength can be represented by the ultrasound flow rate returned by the ultrasonic probe. The gain refers to the magnification of a signal. The preset value may be set as required. If the signal strength value is greater than the preset value, at least one of the gain, the brightness, and the contrast of the ultrasound image is decreased; and if the signal strength value is less than the preset value, at least one of the gain, the brightness, and the contrast of the ultrasound image is increased. As such, the ultrasound image is sharper. The corresponding relationship between the signal strength value and the decreased values of the gain, brightness, and contrast can be set as required. The corresponding relationship between the signal strength value and the increased value of the gain, brightness, and contrast can be set as required. Alternatively, at least one of the gain, the brightness, and the contrast may be decreased or increased based on a preset speed, until a stop instruction input by a user is received.

In an embodiment, the processor 103 may further optimize time gain control (TGC) corresponding to the ultrasound image according to the signal strength value of the ultrasound image. Since the ultrasound intensity decreases with the increase of the detection depth, resulting in transmitted echoes at different depths having unequal intensities, different gain compensations can be given to the echoes at different depths. If the signal strength value is greater than the preset value, it indicates that the required gain compensation is small, and then the gain compensation for the ultrasound image is reduced; and if the signal strength value is less than the preset value, the gain compensation for the ultrasound image is increased.

Figure 8:
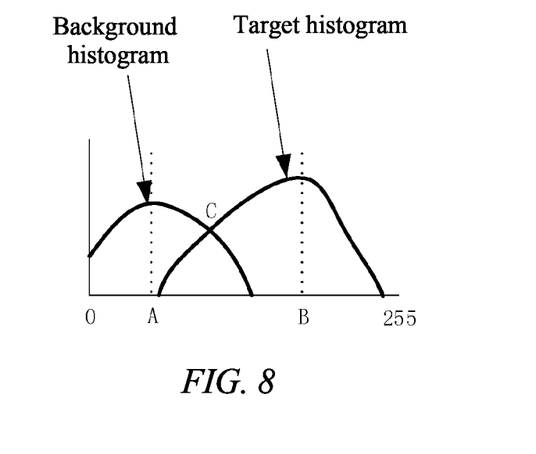
FIG. 8 is a schematic diagram of a grayscale histogram in one embodiment.

In an embodiment, the processor 103 may further determine a background distinguishing grayscale threshold for distinguishing the target anatomical structure from the background according to the grayscale values of the target anatomical structure and the non-target anatomical structure region. After the background distinguishing grayscale threshold is obtained, a region having a grayscale greater than the background distinguishing grayscale threshold is rendered to obtain an ultrasound image, and a region having a grayscale less than the background distinguishing grayscale threshold is usually considered as a background or noise region and will not be rendered. Grayscale distribution data of the target anatomical structure and grayscale distribution data of the non-target anatomical structure region can be obtained, so as to determine the background distinguishing threshold according thereto.

As shown in FIG. 8, corresponding grayscale histograms can be respectively obtained according to the grayscale distribution data of the target anatomical structure and the grayscale distribution data of the non-target anatomical structure region, wherein the abscissa of the grayscale histogram is the grayscale value, and the ordinate thereof is the number of pixels. An intersection of the two histograms (point C in the figure) is selected as a threshold; alternatively, a peak value of the grayscale histogram corresponding to the non-target anatomical structure region (point A in the figure) and a peak value of the target anatomical structure region (point B in the figure) can be respectively calculated, and then a peak grayscale corresponding to point A and a peak grayscale corresponding to point B are subjected to a weighted summation to obtain a background distinguishing grayscale threshold, which may be expressed as follows: $T=a*A+(1-a)*B$, wherein a is a preset weighting coefficient, which may be specifically set as required, for example, a is 0.5.

In an embodiment, the grayscale histogram may be subjected to smoothing processing. For the smoothing processing method, a Gaussian smoothing method may be used to reduce the influence of the random fluctuation of a grayscale value of an ultrasound image on the grayscale distribution data.

Figure 9:
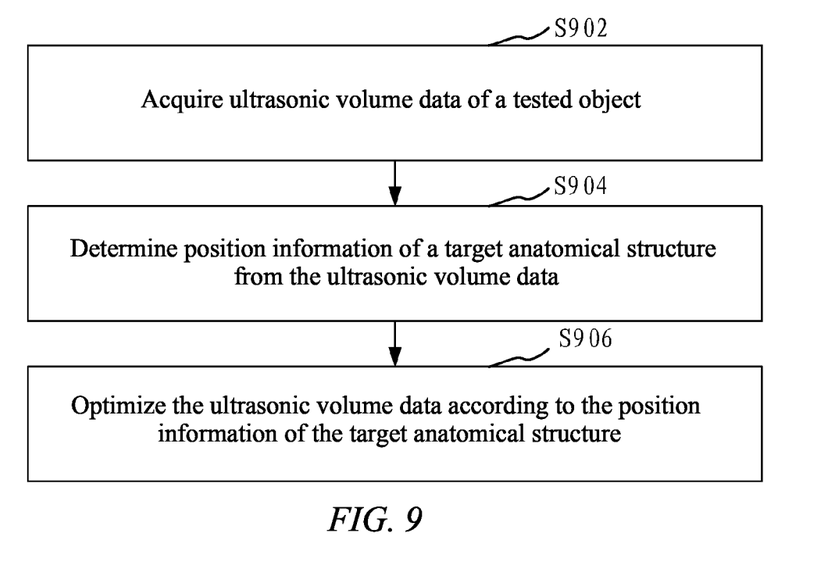
FIG. 9 is a flowchart of a method for optimizing the ultrasound volume data in one embodiment.

As shown in FIG. 9, in an embodiment, a method for optimizing ultrasound volume data is provided, which may specifically comprise the following steps:

step S902: obtaining ultrasound volume data of an object;
step S904: determining position information of a target anatomical structure from the ultrasound volume data; and
step S906: optimizing the ultrasound volume data according to the position information of the target anatomical structure.

In the embodiment of the present disclosure, reference may be made to the corresponding description in any of the above embodiments for the implementation method of steps S902 to S906, which will not be described again in the present disclosure. Since the ultrasound volume data can be optimized according to the position of the target anatomical structure, the time for optimizing the ultrasound volume data is reduced, and ultrasound instrument resources are saved.

Figure 10:
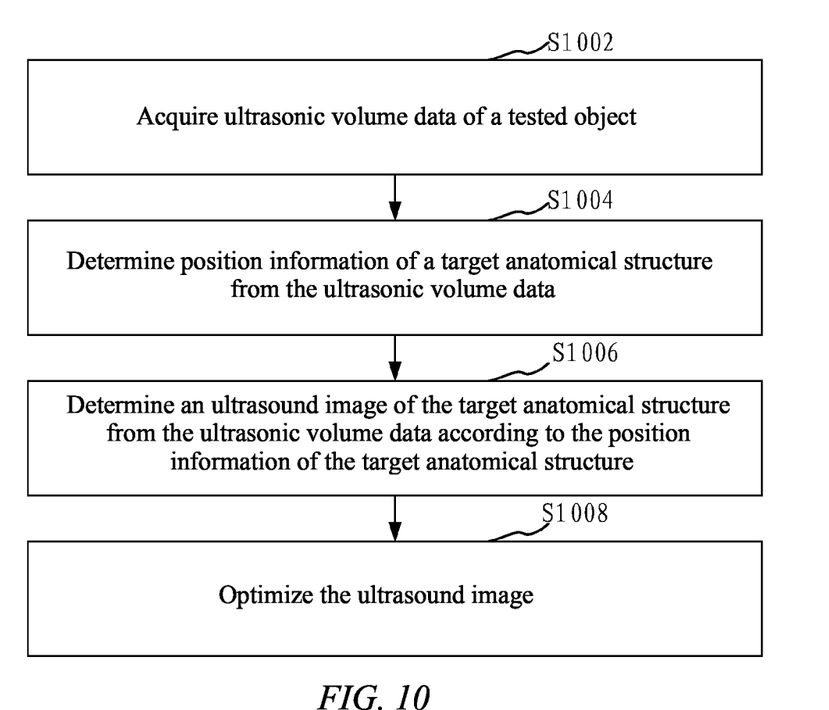
FIG. 10 is a flowchart of a method for optimizing the ultrasound image in one embodiment.

As shown in FIG. 10, in an embodiment, a method for optimizing an ultrasound image is provided, which may specifically comprise the following steps:

step S1002: obtaining ultrasound volume data of an object;
step S1004: determining position information of a target anatomical structure from the ultrasound volume data;
step S1006: determining an ultrasound image of the target anatomical structure from the ultrasound volume data according to the position information of the target anatomical structure;
and step S1008: optimizing the ultrasound image.

In the embodiment of the present disclosure, reference may be made to the corresponding description in any of the above embodiments for the implementation method of steps S1002 to S1008, which will not be described again in the present disclosure.

Figure 11:
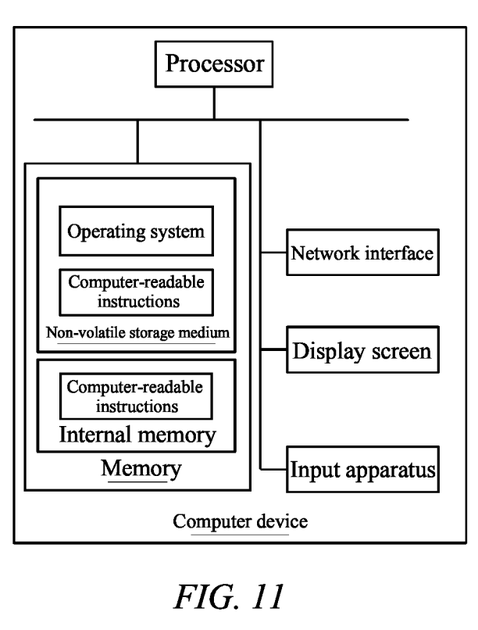
FIG. 11 is a block diagram of an internal structure of a computer device in one embodiment.

FIG. 11 shows an internal structural diagram of a computer device in an embodiment. As shown in FIG. 11, the computer device comprises a processor, a memory, a network interface, an input system and a display screen which are connected by a system bus. The memory comprises a non-volatile storage medium and an internal memory. The non-volatile storage medium of the computer device stores an operating system, and may also store computer-readable instructions that, when executed by the processor, may cause the processor to implement an ultrasound imaging method, a method for optimizing an ultrasound image, and a method for optimizing ultrasound volume data. The internal memory may also store computer-readable instructions that, when executed by the processor, may cause the processor to perform an ultrasound imaging method, a method for optimizing an ultrasound image, and a method for optimizing ultrasound volume data. The display screen of the computer device may be a liquid crystal display screen or an electronic ink display screen. The input system of the computer device may be a touch layer covering the display screen, or may be a button, a trackball or a touchpad arranged on a housing of the computer device, or may be an external keyboard, touchpad, or mouse, etc.

Those skilled in the art may understand that the structure shown in FIG. 11 is merely a block diagram of part of the structure related to the solution of the present disclosure and does not constitute a limitation on the computer device to which the solution of the present disclosure is applied. The specific computer device may comprise more or fewer components than those shown in the figures, or combine some components, or have different component arrangements.

Those of ordinary skill in the art can understand that all or some of the procedures of the methods in the above embodiments can be implemented by computer-readable instructions instructing related hardware. The computer-readable instructions may be stored in a non-volatile computer-readable storage medium, and the computer-readable storage medium, when executed, may comprise the procedures of the embodiments of the methods described above. Any reference to a memory, a storage, a database or other media used in various embodiments provided in the present disclosure may comprise a non-volatile and/or volatile memory. The non-volatile memory may comprise a read only memory (ROM), a programmable ROM (PROM), an electrically programmable ROM (EPROM), an electrically erasable programmable ROM (EEPROM), or a flash memory. The volatile memory may comprise a random access memory (RAM) or an external cache memory. By way of illustration and not limitation, the RAM is available in a plurality of forms, such as a static RAM (SRAM), a dynamic RAM (DRAM), a synchronous DRAM (SDRAM), a double data rate SDRAM (DDRSDRAM), an enhanced SDRAM (ESDRAM), a Synchlink DRAM (SLDRAM), a Rambus direct RAM (RDRAM), a direct Rambus dynamic RAM (DRDRAM), and a Rambus dynamic RAM (RDRAM).

The various technical features of the embodiments described above can be arbitrarily combined. In order to simplify the description, all possible combinations of the various technical features in the above embodiments have not been described. However, any combination of these technical features should be considered to fall with the scope of the disclosure of this description as long as there is no contradiction.

The above embodiments merely represent several implementations of the present disclosure, giving specifics and details thereof, but should not be understood as limiting the scope of the present disclosure thereby. It should be noted that those of ordinary skill in the art could also make several alterations and improvements without departing from the spirit of the present disclosure and these would all fall within the scope of protection of the present disclosure. Therefore, the scope of protection of the present disclosure shall be in accordance with the appended claims.

The invention claimed is:

1. An ultrasound imaging method, comprising:
   acquiring, by a processor, an ultrasound volume data of an object with an ultrasonic probe;
   automatically determining, by the processor using a machine learning model, position information of a target anatomical structure from the ultrasound volume data, wherein the machine learning model is a learning model obtained by training based on one or more of an Adaboost algorithm, a support vector machine (SVM), a neural network algorithm, a convolutional neural network (CNN) algorithm, a recursive neural network (RNN) algorithm, a fast region-based convolutional network (RCNN), and a single shot multibox detector (SSD);
   determining, by the processor, an ultrasound image of the target anatomical structure from the ultrasound volume data according to the position information of the target anatomical structure, wherein the ultrasound image of the target anatomical structure comprises at least one of: an ultrasound image of a section corresponding to the target anatomical structure and an ultrasound image of a volume of interest (VOI) corresponding to the target anatomical structure; and
   displaying, by the processor, the ultrasound image of the target anatomical structure on a display device, wherein in response to the ultrasound image of the target anatomical structure comprising the ultrasound image of the VOI corresponding to the target anatomical structure, determining, by the processor, the ultrasound image of the target anatomical structure from the ultrasound volume data according to the position information of the target anatomical structure comprises:
   determining position information of a target section according to the position information of the target anatomical structure; and
   setting a size and position information of the VOI corresponding to the target anatomical structure in the ultrasound volume data according to the position information of the target section, comprising:
   automatically setting a proportion of a volume surrounded by the VOI corresponding to the target anatomical structure to a total volume of the target anatomical structure to be greater than a preset volume threshold, wherein the size of the VOI corresponding to the target anatomical structure comprises length, width, and height, and the VOI corresponding to the target anatomical structure contains all or part of the target anatomical structure; and
   rendering the VOI corresponding to the target anatomical structure to obtain a stereoscopic image of the target anatomical structure as the ultrasound image of the VOI corresponding to the target anatomical structure.

2. The method of claim 1, wherein in response to the ultrasound image of the target anatomical structure comprising the ultrasound image of the section corresponding to the target anatomical structure, determining, by the processor, the ultrasound image of the target anatomical structure from the ultrasound volume data according to the position information of the target anatomical structure comprises:
   determining a section image of the target anatomical structure from the ultrasound volume data according to the position information of the target section as the ultrasound image of the section corresponding to the target anatomical structure.

3. The method of claim 2, wherein determining the position information of the target section according to the position information of the target anatomical structure comprises:
   determining an equation of the target section according to the position information of the target anatomical structure, comprising:
   selecting feature points from the target anatomical structure;
   substituting position information of the feature points into a plane equation to solve plane parameters; and
   obtain a section function corresponding to the target section based on the plane parameters, wherein the section function is used to obtain a region corresponding to the section function from ultrasound volume data; and
   obtaining the position information of the target section according to the equation of the target section.

4. The method of claim 3, wherein determining the equation of the target section according to the position information of the target anatomical structure comprises:
   determining the equation of the target section according to the position information of the target anatomical structure through three non-collinear points.

5. The method of claim 3, wherein determining the equation of the target section according to the position information of the target anatomical structure comprises:
   determining the equation of the target section according to the position information of the target anatomical structure through a fitting, wherein the fitting comprises at least one of a least squares estimation and a Hough transform.

6. The method of claim 1, wherein automatically determining, by the processor using a machine learning model, the position information of the target anatomical structure from the ultrasound volume data comprises:
   obtaining a structural feature information of the target anatomical structure; and
   determining the position information of the target anatomical structure from the ultrasound volume data according to the structural feature information.

7. The method of claim 1, after automatically determining, by the processor using a machine learning model, the position information of the target anatomical structure from the ultrasound volume data, further comprising:

optimizing the ultrasound volume data according to the position information of the target anatomical structure.

8. The method of claim 7, wherein optimizing the ultrasound volume data according to the position information of the target anatomical structure comprises:
  decreasing an ultrasound volume data parameter value of a non-target anatomical structure region according to the position information of the target anatomical structure, such that a difference between an ultrasound volume data parameter value of the target anatomical structure and the ultrasound volume data parameter value of the non-target anatomical structure region is within a preset range, wherein the non-target anatomical structure region is a region other than the target anatomical structure in the ultrasound volume data.

9. The method of claim 7, wherein optimizing the ultrasound volume data according to the position information of the target anatomical structure comprises:
  obtaining ultrasound volume data parameter values of the target anatomical structure and a non-target anatomical structure region according to the position information of the target anatomical structure, wherein the non-target anatomical structure region is a region other than the target anatomical structure in the ultrasound volume data; and
  adjusting the ultrasound volume data parameter values of the target anatomical structure and the non-target anatomical structure region according to a preset condition.

10. The method of claim 1, after determining, by the processor, the ultrasound image of the target anatomical structure from the ultrasound volume data according to the position information of the target anatomical structure, further comprising:
  optimizing the ultrasound image of the target anatomical structure.

11. The method of claim 10, wherein optimizing the ultrasound image of the target anatomical structure comprises:
  optimizing at least one of a threshold, a gain, a brightness and a contrast of the ultrasound image of the target anatomical structure, wherein, the threshold is a difference between grayscale values of the target anatomical structure and a non-target anatomical structure region, and the non-target anatomical structure region is a region other than the target anatomical structure in the ultrasound volume data.

12. The method of claim 11, wherein optimizing the threshold of the ultrasound image of the target anatomical structure comprises:
  obtaining the threshold of the ultrasound image of the target anatomical structure; and
  adjusting the threshold of the ultrasound image of the target anatomical structure when the threshold of the ultrasound image of the target anatomical structure is not in a preset threshold range.

13. The method of claim 11, wherein optimizing at least one of the gain, the brightness and the contrast of the ultrasound image of the target anatomical structure comprises:
  obtaining a signal strength value of the ultrasound image of the target anatomical structure; and
  decreasing at least one of the gain, the brightness, and the contrast of the ultrasound image of the target anatomical structure when the signal strength value is greater than a preset value, or increasing at least one of the gain, the brightness, and the contrast of the ultrasound image of the target anatomical structure when the signal strength value is less than a preset value.

14. A method for optimizing ultrasound volume data, comprising:
  acquiring, by a processor, an ultrasound volume data of an object with an ultrasonic probe;
  automatically determining, by the processor using a machine learning model, position information of a target anatomical structure from the ultrasound volume data, wherein the machine learning model is a learning model obtained by training based on one or more of an Adaboost algorithm, a support vector machine (SVM), a neural network algorithm, a convolutional neural network (CNN) algorithm, a recursive neural network (RNN) algorithm, a fast region-based convolutional network (RCNN), and a single shot multibox detector (SSD);
  determining, by the processor, an ultrasound image of the target anatomical structure from the ultrasound volume data according to the position information of the target anatomical structure, wherein the ultrasound image of the target anatomical structure comprises at least one of: an ultrasound image of a section corresponding to the target anatomical structure and an ultrasound image of a volume of interest (VOI) corresponding to the target anatomical structure; and
  optimizing, by the processor, the ultrasound volume data according to the position information of the target anatomical structure;
  displaying, by the processor, the ultrasound image of the target anatomical structure on a display device according to the optimized ultrasound volume data;
  wherein in response to the ultrasound image of the target anatomical structure comprising the ultrasound image of the VOI corresponding to the target anatomical structure, determining, by the processor, the ultrasound image of the target anatomical structure from the ultrasound volume data according to the position information of the target anatomical structure comprises:
    determining position information of a target section according to the position information of the target anatomical structure; and
    setting a size and position information of the VOI corresponding to the target anatomical structure in the ultrasound volume data according to the position information of the target section, comprising:
      automatically setting a proportion of a volume surrounded by the VOI corresponding to the target anatomical structure to a total volume of the target anatomical structure to be greater than a preset volume threshold, wherein the size of the VOI corresponding to the target anatomical structure comprises length, width, and height, and the VOI corresponding to the target anatomical structure contains all or part of the target anatomical structure; and
      rendering the VOI corresponding to the target anatomical structure to obtain a stereoscopic image of the target anatomical structure as the ultrasound image of the VOI corresponding to the target anatomical structure.

15. The method of claim 14, wherein optimizing, by the processor, the ultrasound volume data according to the position information of the target anatomical structure comprises:
  decreasing an ultrasound volume data parameter value of a non-target anatomical structure region according to the position information of the target anatomical structure, such that a difference between an ultrasound volume data parameter value of the target anatomical structure and the ultrasound volume data parameter value of the non-target anatomical structure region is within a preset range, wherein the non-target anatomical structure region is a region other than the target anatomical structure in the ultrasound volume data.

16. The method of claim 14, wherein optimizing, by the processor, the ultrasound volume data according to the position information of the target anatomical structure comprises:

obtaining ultrasound volume data parameter values of the target anatomical structure and a non-target anatomical structure region according to the position information of the target anatomical structure, wherein the non-target anatomical structure region is a region other than the target anatomical structure in the ultrasound volume data; and adjusting the ultrasound volume data parameter values of the target anatomical structure and the non-target anatomical structure region according to a preset condition.

17. A method for optimizing an ultrasound image, comprising:

acquiring, by a processor, an ultrasound volume data of an object with an ultrasonic probe;

automatically determining, by the processor using a machine learning model, position information of a target anatomical structure from the ultrasound volume data, wherein the machine learning model is a learning model obtained by training based on one or more of an Adaboost algorithm, a support vector machine (SVM), a neural network algorithm, a convolutional neural network (CNN) algorithm, a recursive neural network (RNN) algorithm, a fast region-based convolutional network (RCNN), and a single shot multibox detector (SSD);

determining, by the processor, an ultrasound image of the target anatomical structure from the ultrasound volume data according to the position information of the target anatomical structure, wherein the ultrasound image of the target anatomical structure comprises at least one of: an ultrasound image of a section corresponding to the target anatomical structure and an ultrasound image of a volume of interest (VOI) corresponding to the target anatomical structure; and optimizing, by the processor, the ultrasound image of the target anatomical structure, wherein in response to the ultrasound image of the target anatomical structure comprising the ultrasound image of the VOI corresponding to the target anatomical structure, determining, by the processor, the ultrasound image of the target anatomical structure from the ultrasound volume data according to the position information of the target anatomical structure comprises:

determining position information of a target section according to the position information of the target anatomical structure; and setting a size and position information of the VOI corresponding to the target anatomical structure in the ultrasound volume data according to the position information of the target section, comprising:

automatically setting a proportion of a volume surrounded by the VOI corresponding to the target anatomical structure to a total volume of the target anatomical structure to be greater than a preset volume threshold, wherein the size of the VOI corresponding to the target anatomical structure comprises length, width, and height, and the VOI corresponding to the target anatomical structure contains all or part of the target anatomical structure; and rendering the VOI corresponding to the target anatomical structure to obtain a stereoscopic image of the target anatomical structure as the ultrasound image of the VOI corresponding to the target anatomical structure.

18. The method of claim 2, wherein determining the position information of the target section according to the position information of the target anatomical structure comprises:

traversing to obtain candidate sections that pass through the target anatomical structure; and selecting, from the candidate sections, a candidate section comprising a largest region of the target anatomical structure as the target section.

* * * * *